(12) United States Patent
Long et al.

(10) Patent No.: US 11,576,822 B2
(45) Date of Patent: Feb. 14, 2023

(54) APPARATUSES AND METHODS FOR MAKING ABSORBENT ARTICLES

(71) Applicant: The Procter & Gamble Company, Cincinnati, OH (US)

(72) Inventors: Michael Devin Long, Harrison Township, OH (US); Uwe Schneider, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 214 days.

(21) Appl. No.: 17/019,412

(22) Filed: Sep. 14, 2020

(65) Prior Publication Data

US 2021/0077307 A1 Mar. 18, 2021

Related U.S. Application Data

(60) Provisional application No. 62/901,361, filed on Sep. 17, 2019.

(51) Int. Cl.
*A61F 13/15* (2006.01)
*B32B 38/00* (2006.01)

(52) U.S. Cl.
CPC .......... *A61F 13/15577* (2013.01); *A61F 2013/15869* (2013.01); *A61F 2013/15934* (2013.01); *B32B 38/0004* (2013.01)

(58) Field of Classification Search
CPC ...... A61F 13/15577; A61F 2013/15869; A61F 2013/15934; A61F 13/62; A61F 13/622; B29L 2031/729; B32B 38/0004
See application file for complete search history.

(56) References Cited

U.S. PATENT DOCUMENTS 8,079,995 B2 * 12/2011 Tachauer .............. B29C 43/222
604/367
2006/0246256 A1 * 11/2006 Ausen ................ A44B 18/0034
428/100

(Continued)

FOREIGN PATENT DOCUMENTS

EP 0381087 A1 8/1990
GB 2311096 A 9/1997

OTHER PUBLICATIONS

International Search Report and Written Opinion; Application Ser. No. PCT/US2020/070536; dated Dec. 23, 2020, 13 pages.

*Primary Examiner* — Michael A Tolin
*Assistant Examiner* — Christopher C Caillouet
(74) *Attorney, Agent, or Firm* — Amanda Herman Berghauer; Christian M. Best; Christopher Brant Cook

(57) ABSTRACT

Aspects of the present disclosure relate to methods and apparatuses for manufacturing absorbent articles, wherein discrete zones of protrusions may be formed on a substrate. In some configurations, the protrusions may be formed as hooks. When forming the discrete zones of protrusions, localized speed variances may be imparted to the advancing substrate to ensure the adequate time to form the protrusions is provided. As such, protrusions may be formed on portions of the substrate that have been temporarily stopped or slowed to relatively slow speeds. The substrates with zones of protrusions may then be incorporated into products, such as assembled absorbent articles, so as to place the protrusions in desired positions on the absorbent articles. As such, the methods and apparatuses herein allow for the use of hook forming techniques on substrates in article manufacturing processes that provide flexibility in such configurations without sacrificing desired manufacturing speeds.

18 Claims, 10 Drawing Sheets

(56) References Cited

U.S. PATENT DOCUMENTS

| | | | |
|---|---|---|---|
| 2010/0180407 A1* | 7/2010 | Rocha | B29C 59/04 |
| | | | 264/444 |
| 2010/0239699 A1* | 9/2010 | Banker | A44B 18/0049 |
| | | | 425/115 |
| 2013/0280474 A1* | 10/2013 | Medina | B32B 3/06 |
| | | | 156/243 |
| 2016/0220423 A1 | 8/2016 | Schneider et al. | |
| 2018/0228669 A1* | 8/2018 | Schneider | A61F 13/49 |

* cited by examiner

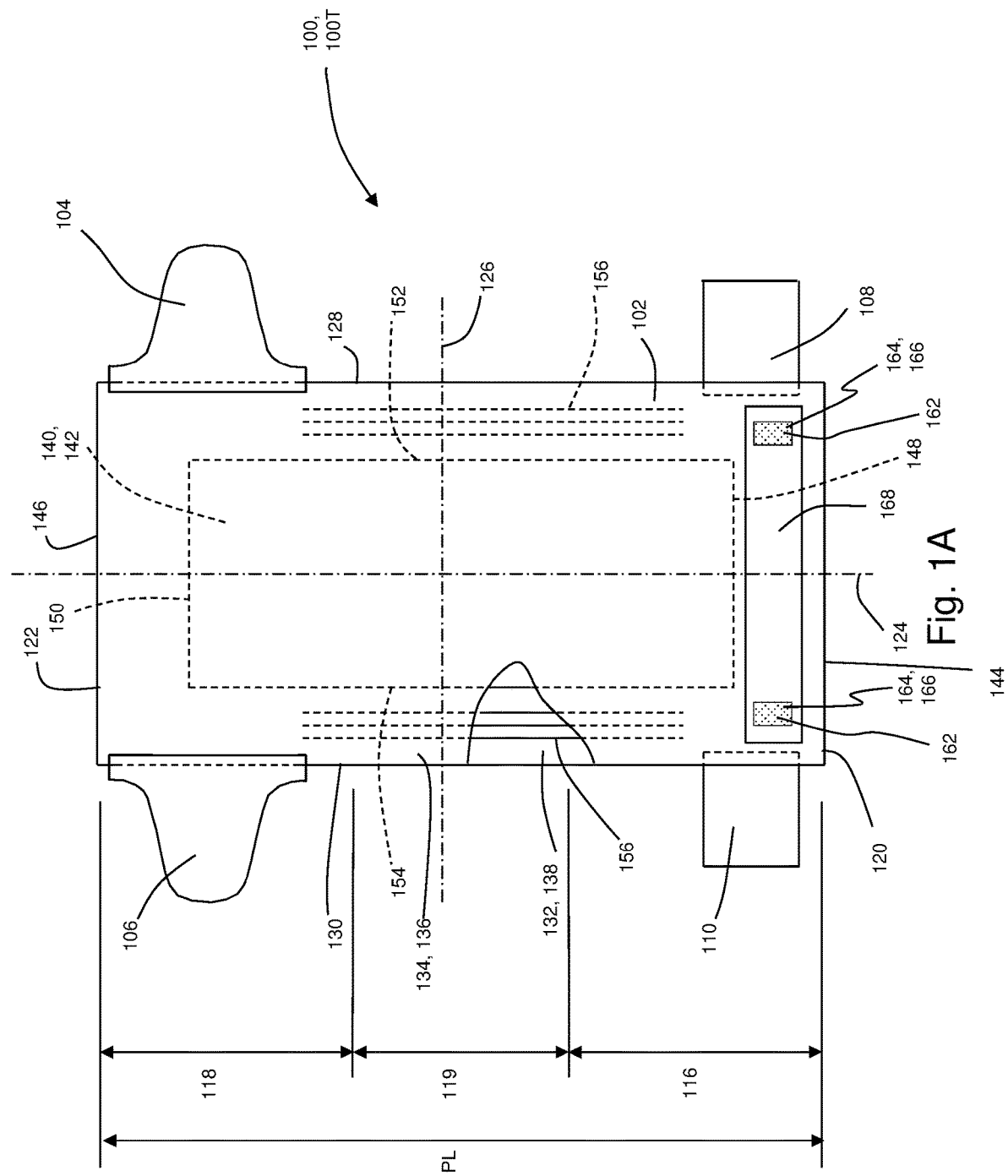

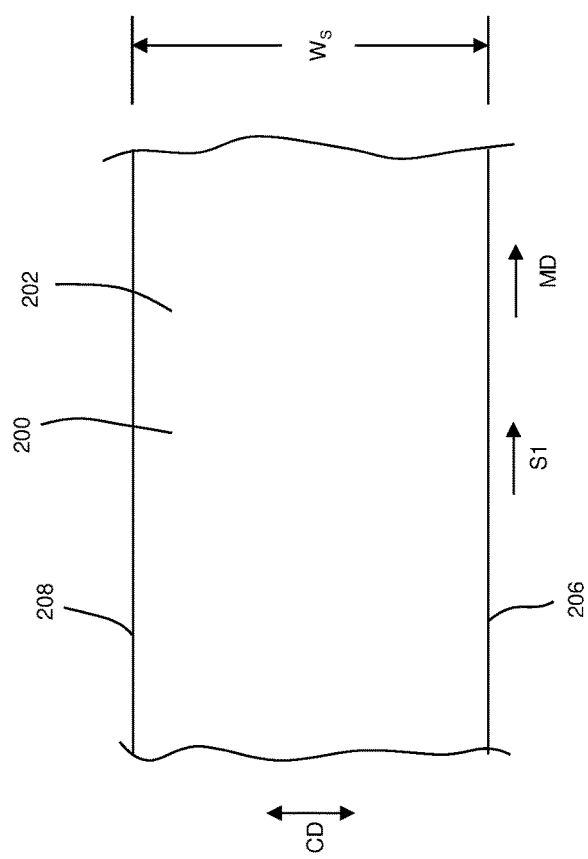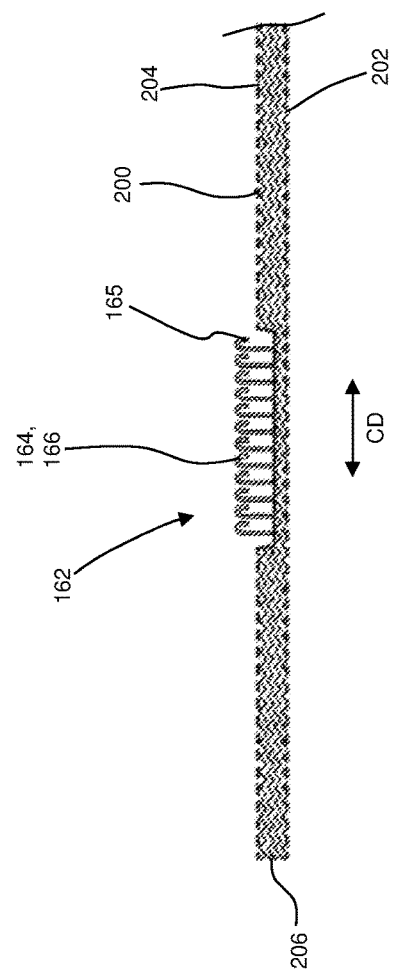

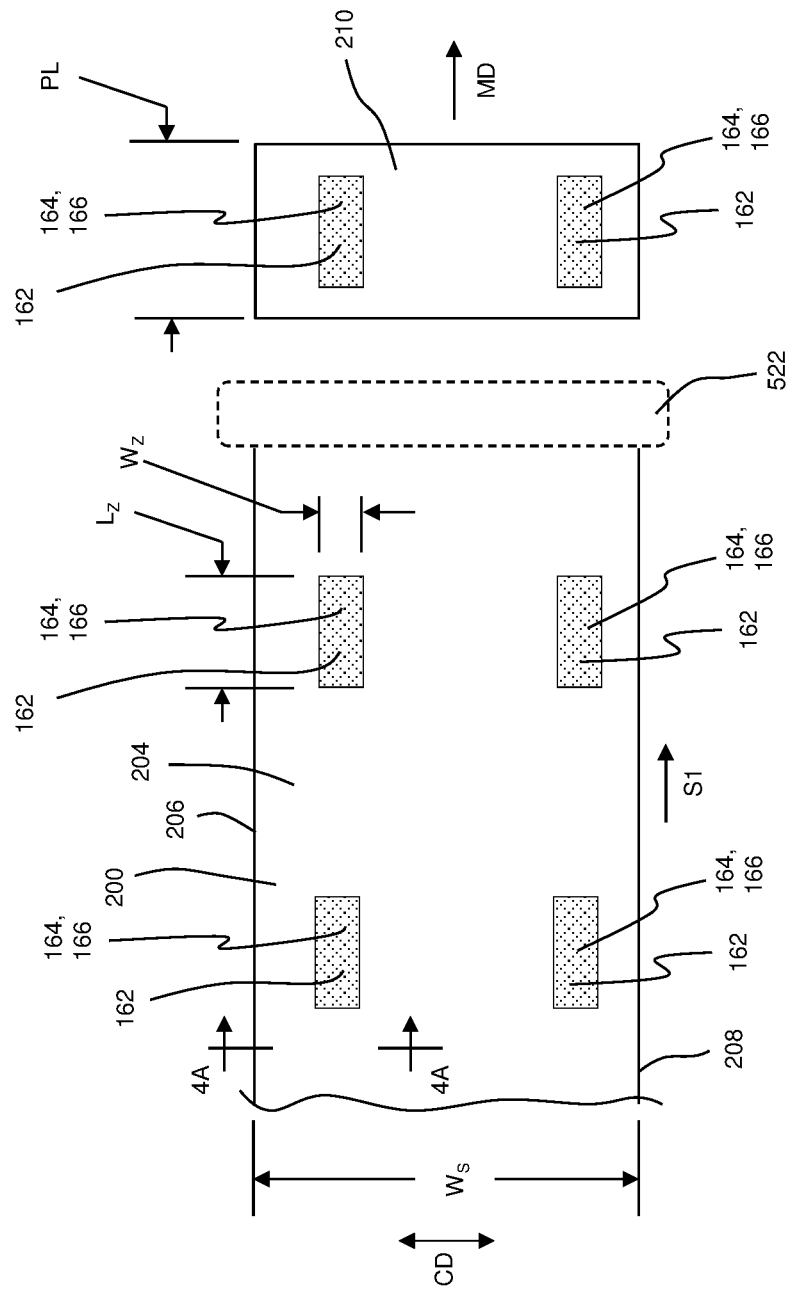

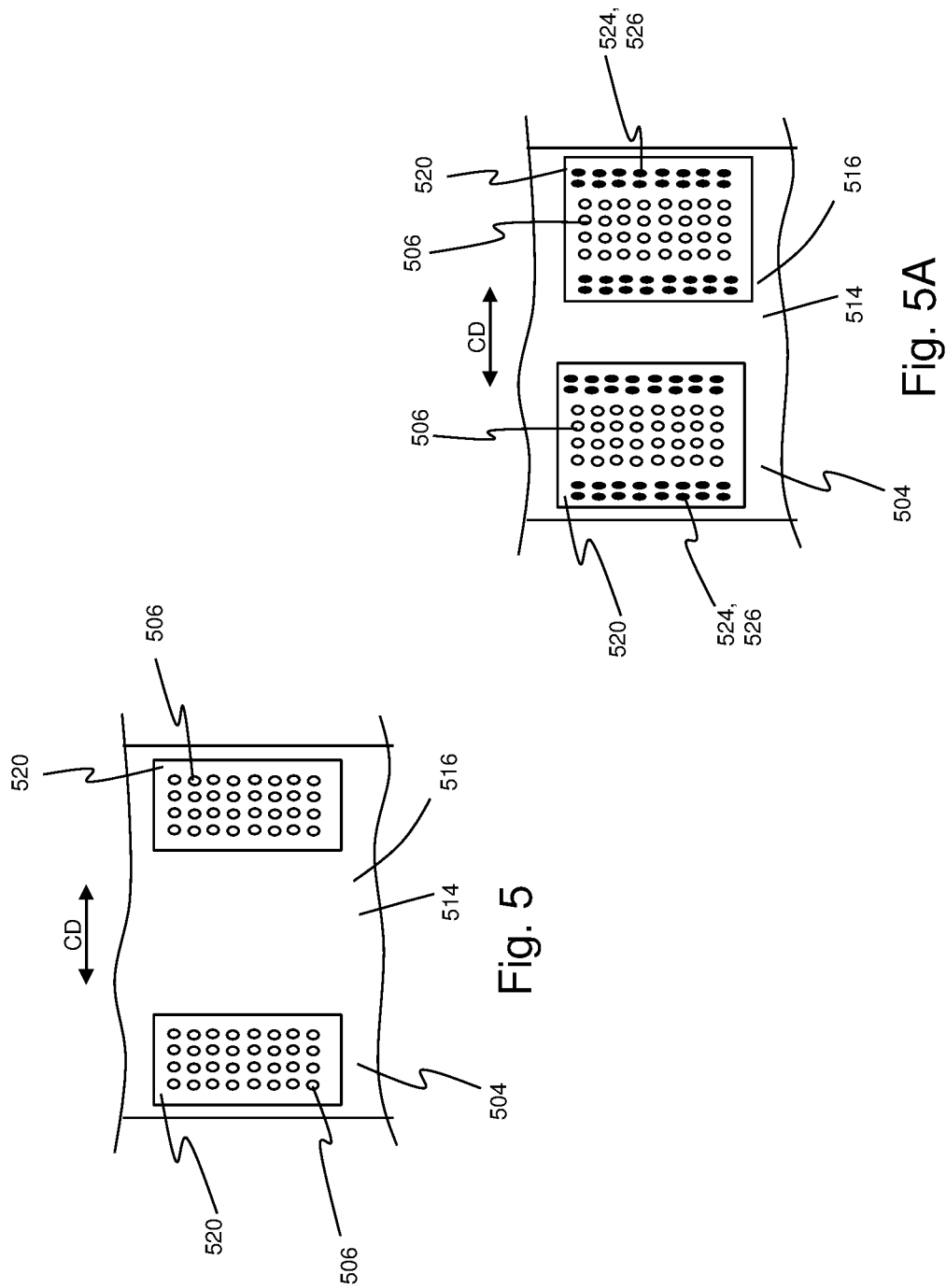

APPARATUSES AND METHODS FOR MAKING ABSORBENT ARTICLES

FIELD OF THE INVENTION

The present disclosure relates to methods for manufacturing absorbent articles, and more particularly, to apparatuses and methods of forming discrete zones of hooks on a substrate while imparting localized speed variances to the substrate while advancing in a machine direction.

BACKGROUND OF THE INVENTION

Fastening systems for connecting or holding together portions of garment materials are available in various different forms, including buttons, snap fasteners, tape tab fasteners, hook-and-loop fasteners, and the like. Such fastening systems may be utilized on garments and disposable garments, such as absorbent articles, body wraps, bibs, bedsheets, tablecloths and the like. In the field of absorbent articles, such as disposable diapers and feminine protection devices, various types of fasteners may be provided to hold cooperating portions of a structure in a desired spatial relationship. Disposable diapers, for example, may include a fastener system in the form of a hook-and-loop fastening system.

In some configurations, a disposable diaper and fastening system may include an absorbent chassis having a front waist region, crotch region and rear waist region, with a pair of fastening members each extending respectively laterally from left and right longitudinal edges of the chassis in the rear waist region. Each fastening member may include a patch of material bearing hooks, affixed to a wearer-facing side of the fastening member. A patch or section of cooperating loops material may be disposed on an outward-facing side of the front waist region. In such a configuration, the chassis may be wrapped through the wearer's crotch area with the back waist region placed across the wearer's lower back and buttocks and the front waist region placed across the wearer's lower belly area. The left and right fastening members may then be wrapped about the wearer's left and right hips, respectively, and fastened to the front waist region via engagement of the hooks patches with the loops material on the front waist region, thereby securing the diaper on the wearer.

Hooks of various designs for use with various types of loops material have been developed in the past along with techniques for manufacturing hooks. One manufacturing technique has included heating thermoplastic resin in an extruder. A base sheet is extruded, and hooks are then molded and/or otherwise formed into one face of the base sheet from the material thereof, while the material is still soft or partially molten. Another technique has included extruding a continuous structure having a base sheet portion and a series of extruded formations extending from the base sheet portion having desired hook profiles. Following extrusion, a series of cuts through the formations are made along a direction transverse to the extrusion direction to create rows of hooks structures, without cutting through the base portion. The base sheet with rows of hooks structures is then plastically stretched along the extrusion direction, to create or enlarge separation between the rows of hooks structures. In some applications, a layer of suitable adhesive may be applied to the underside of the base material. The combination of hooks, base sheet material, and adhesive may then be cut to any commercially desired size or shape, such as strips. In turn, the strips may be gathered, for example on a roll, to be delivered to a purchaser and/or user. The purchaser and/or user may further cut the product to a desired size, such as a hooks patch that may be affixed to an article and thereby provide the hooks component of a hook-and-loop fastening system for the article.

In an attempt to eliminate various processing and handling steps involved with such hooks materials and manufacture of articles with hook-and-loop fastening systems, other techniques have been developed that enable formation of patterns of hooks directly on a preexisting substrate, such as a film or nonwoven. For example, a substrate may be positioned between a mold and a source of vibration, such as an ultrasonic horn. In turn, the ultrasonic horn may impart vibration energy to soften the substrate. The mold may include a plurality of cavities into which the softened substrate material may be forced to form the hooks. However, the relatively slow speeds associated with such hook forming techniques may create challenges, particularly when such hook forming techniques are incorporated into absorbent article assembly processes operating at relatively high speed production rates. In addition, such methods and apparatuses may not be very flexible in allowing a user to reconfigure so as to accommodate for production of different sized articles and/or different patterns of hooks.

Consequently, it would be beneficial to provide flexible methods and apparatuses for forming hooks on substrates in absorbent article manufacturing processes without sacrificing relatively high manufacturing speeds.

SUMMARY OF THE INVENTION

In one form, a method for assembling absorbent articles comprises steps of: advancing a first substrate in a machine direction at a first speed, the first substrate comprising a first surface and an opposing second surface and defining a width, Ws, in a cross direction; decelerating a portion of the first substrate to a second speed; arranging the second surface of the portion the first substrate and a die surface in a facing relationship, wherein the die surface comprises cavities; applying energy to the portion of the first substrate while advancing at the second speed such that softened material of the first substrate moves into the cavities of the die surface to form a zone of protrusions, wherein the zone of protrusions extends in the machine direction for a length, Lz, and wherein each protrusion protrudes from the second surface of the first substrate to a distal end; accelerating the portion of the first substrate with the zone of protrusions from the second speed to the first speed; and cutting the first substrate into discrete pieces each having a pitch length, PL, extending along the machine direction, wherein the length, Lz, of the zone of protrusions extends in the machine direction for less than the pitch length, PL.

In another form, a method for assembling absorbent articles comprises steps of: advancing a first substrate in a machine direction at a first speed, the first substrate comprising a first surface and an opposing second surface and defining a width, Ws, in a cross direction; decelerating a portion of the first substrate to a second speed; arranging the second surface of the portion the first substrate and a die surface in a facing relationship, wherein the die surface comprises cavities; applying energy to the portion of the first substrate while advancing at the second speed such that softened material of the first substrate moves into the cavities of the die surface to form a zone of protrusions, wherein the zone of protrusions extends in the cross direction for a width, Wz, and wherein each protrusion protrudes from the second surface of the first substrate to a distal end;

accelerating the portion of the first substrate with the zone of protrusions from the second speed to the first speed; and cutting the first substrate into discrete pieces, wherein the width, Wz, of the zone of protrusions extends in the cross direction for a distance that is equal to or less than the width, Ws.

In yet another form, a method for assembling absorbent articles comprises steps of: advancing a first substrate in a machine direction at a first speed, the first substrate comprising a first surface and an opposing second surface and defining a width, W, in a cross direction; decelerating a portion of the first substrate to a second speed; arranging the second surface of the portion the first substrate and a die surface in a facing relationship, wherein the die surface comprises cavities; applying energy to the portion of the first substrate while advancing at the second speed such that softened material of the first substrate moves into the cavities of the die surface to form a zone of protrusions, wherein the zone of protrusions extends in the machine direction for a length, Lz, and wherein each protrusion protrudes from the second surface of the first substrate to a distal end; combining a second substrate with the portion of the first substrate; bonding the second substrate with the portion of the first substrate while at the second speed; accelerating the second substrate and the portion of the first substrate with the zone of protrusions from the second speed to the first speed; and cutting the first substrate into discrete pieces.

BRIEF DESCRIPTION OF THE DRAWINGS

FIG. 1A is a partially cut away plan view of an absorbent article in the form of a taped diaper that may include one or more substrates with protrusions formed thereon in accordance with the present disclosure with the portion of the diaper that faces away from a wearer oriented towards the viewer.

FIG. 3 is a view of an advancing substrate taken along section 3-3 in FIG. 2.

FIG. 4 is a view of the advancing substrate with discrete zones of protrusions taken along section 4-4 in FIG. 2.

FIG. 4A is a cross sectional view of the advancing substrate showing a discrete zone of protrusions taken along section 4A-4A in FIG. 4.

FIG. 5 is a view of a die surface taken along section 5-5 in FIG. 2.

FIG. 5A is a view of a configuration of a die surface including cavities and bonding elements taken along section 5-5 in FIG. 2.

DETAILED DESCRIPTION OF THE INVENTION

Figure 1B:
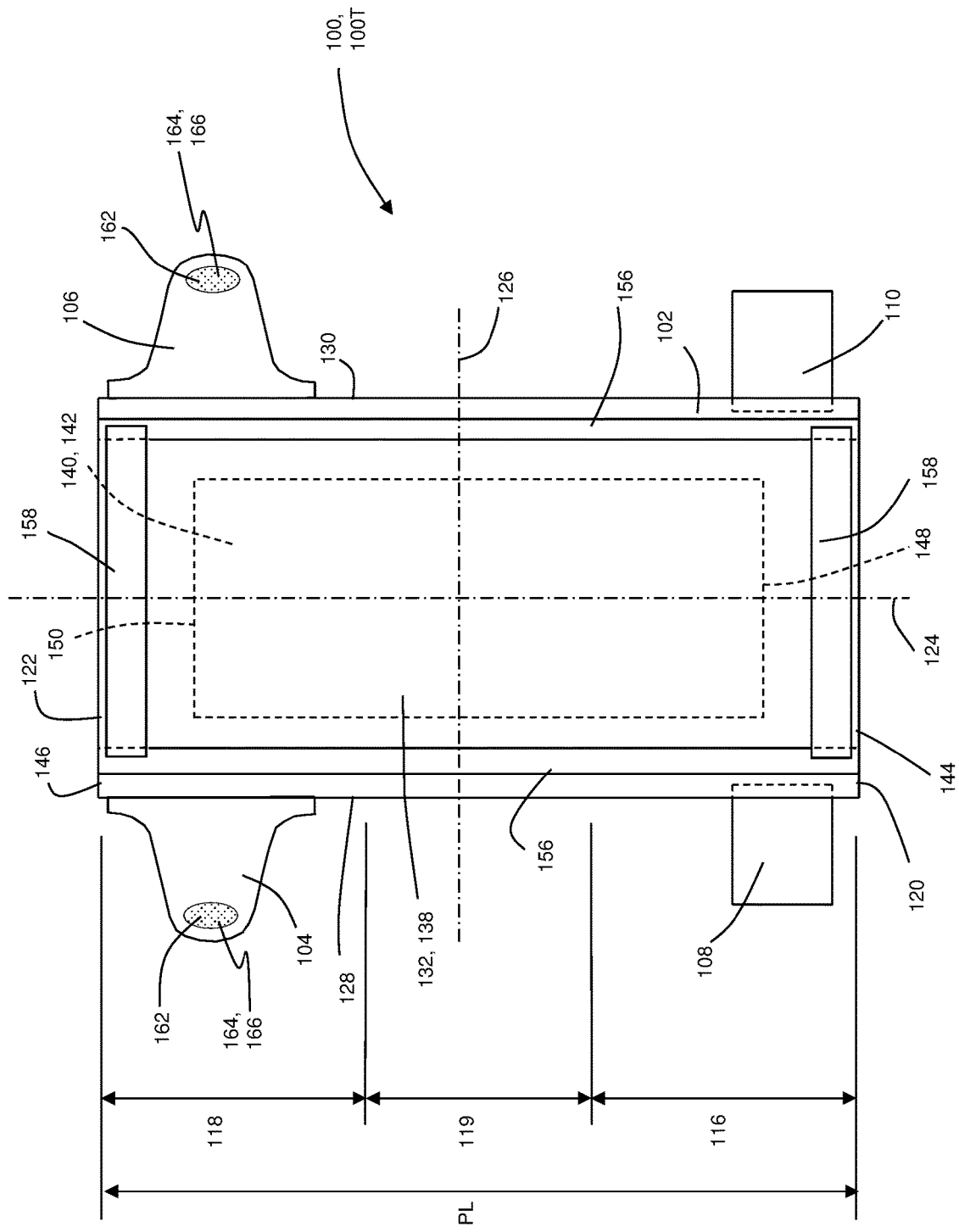
FIG. 1B is a plan view of the absorbent article of FIG. 1A that may include one or more substrates with protrusions formed thereon in accordance with the present disclosure with the portion of the diaper that faces toward a wearer oriented towards the viewer.

The following term explanations may be useful in understanding the present disclosure:

"Absorbent article" is used herein to refer to consumer products whose primary function is to absorb and retain soils and wastes. Absorbent articles can comprise sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "feminine hygiene articles" refers to disposable absorbent articles used by women for catamenial protection. Such feminine hygiene articles may include sanitary napkins, tampons, interlabial products, incontinence devices, and pantiliners. Non-limiting examples of panty liners and sanitary napkins include those disclosed in U.S. Pat. Nos. 4,324,246; 4,463,045; 4,342,314; 4,556,146; 4,589,876; 4,687,478; 4,950,264; 5,009,653; 5,267,992; and 6,004,893, which are all incorporated by reference herein.

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "graphic" refers to images or designs that are constituted by a figure (e.g., a line(s)), a symbol or character, a color difference or transition of at least two colors, or the like. A graphic may include an aesthetic image or design that can provide certain benefit(s) when viewed. A graphic may be in the form of a photographic image. A graphic may also be in the form of a 1-dimensional (1-D) or 2-dimensional (2-D) bar code or a quick response (QR) bar code. A graphic design is determined by, for example, the color(s) used in the graphic (individual pure ink or spot colors as well as built process colors), the sizes of the entire graphic (or components of the graphic), the positions of the graphic (or components of the graphic), the movements of the graphic (or components of the graphic), the geometrical shapes of the graphic (or components of the graphics), the number of colors in the graphic, the variations of the color combinations in the graphic, the number of graphics printed, the disappearance of color(s) in the graphic, and the contents of text messages in the graphic.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. $\frac{1}{10}$ or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. In some configurations, a nonwoven may comprise a polyolefin based nonwoven, including but not limited to nonwovens having polypropylene fibers and/or polyethylene fibers and/or bicomponent fibers comprising a polyolefin. Nonlimiting examples of suitable fibers include spunbond, spunlaid, meltblown, spunmelt, solvent-spun, electrospun, carded, film fibrillated, melt-film fibrillated, air-laid, dry-laid, wet-laid staple fibers, and other nonwoven web materials formed in part or in whole of polymer fibers as known in the art, and workable combinations thereof. Nonwovens do not have a woven or knitted filament pattern. It is to be appreciated that nonwovens having various basis weights can be used in accordance with the methods herein. For example, some nonwovens may have a basis weight of at least about 8 gsm, 12 gsm, 16 gsm, 20 gsm, 25 gsm, 25 gsm, 40 gsm, or 65 gsm. Some nonwovens may have basis weight of about 8 gsm to about 65 gsm, specifically reciting all 1 gsm increments within the above-recited ranges and all ranges formed therein or thereby.

It is to be appreciated that films having various basis weights can be used in accordance with the methods herein. For example, some films may have a basis weight of at least about 8 gsm, 12 gsm, 16 gsm, 20 gsm, 25 gsm, 25 gsm, 40 gsm, or 60 gsm. Some films may have basis weight of about 8 gsm to about 60 gsm, specifically reciting all 1 gsm increments within the above-recited ranges and all ranges formed therein or thereby.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

Aspects of the present disclosure relate to methods and apparatuses for manufacturing absorbent articles, and more particularly, to forming discrete zones of protrusions on a substrate. In some configurations, the protrusions may be formed as hooks. When forming the discrete zones of protrusions, localized speed variances may be imparted to the advancing substrate to ensure the necessary time to form the protrusions is provided. As such, protrusions may be formed on portions of the substrate that have been temporarily stopped or slowed to relatively slow speeds. The substrates with zones of protrusions may then be incorporated into assembled absorbent articles so as to place the protrusions in desired positions on the absorbent articles. As such, the methods and apparatuses herein allow for the use of hook forming techniques on substrates in diaper manufacturing processes that provide flexibility in such configurations without sacrificing relatively high manufacturing speeds.

With regard to the assembly processes described herein, a continuous substrate may be advanced in a machine direction at a first speed, the substrate comprising a first surface and an opposing second surface, and defining a width, Ws, in a cross direction. A portion of the substrate is decelerated to a second speed. While at the second speed, the second surface of the portion the first substrate and a die surface are arranged in a facing relationship, wherein the die surface comprises cavities. Energy is applied to the portion of the substrate while advancing at the second speed such that softened material of the substrate moves into the cavities of the die surface to form a zone of protrusions. Each protrusion protrudes from the second surface of the substrate to a distal end. The zone of protrusions extends in the machine direction MD for a length, Lz, and extends in the cross direction CD for a width, Wz. The portion of the substrate with the zone of protrusions is then accelerated from the second speed to the first speed. The substrate having the zone of protrusions may then be cut into discrete pieces each having a pitch length, PL, extending along the machine direction, wherein the length, Lz, of the zone of protrusions extends in the machine direction for less than the pitch length, PL. The width, Wz, of the zone of protrusions may also extend in the cross direction for a distance that is equal to or less than the width, Ws, of the substrate. As discussed in more detail below, the substrate may be subject to additional operations while advancing at the second speed, such as for example, bonding with other substrates and/or printing operations.

It is to be appreciated that the systems and methods disclosed herein are applicable to work with various types of converting processes and/or machines, such as for example, absorbent article manufacturing and assembly processes. The methods and apparatuses are discussed below in the context of manufacturing diapers that may be configured as taped diapers or pant diapers.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, which are all incorporated by reference herein.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897,545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

For the purposes of a specific illustration, FIGS. 1A and 1B show an example of an absorbent article 100 that may be assembled in accordance with the methods and apparatuses disclosed herein. In particular, FIG. 1A shows one example of a plan view of an absorbent article 100 configured as a taped diaper 100T, with the portion of the diaper that faces away from a wearer oriented towards the viewer. And FIG. 1B shows a plan view of the diaper 100 with the portion of the diaper that faces toward a wearer oriented towards the viewer. The taped diaper 100T shown in FIGS. 1A and 1B includes an absorbent chassis 102, first and second rear side panels 104 and 106; and first and second front side panels 108 and 110.

As shown in FIGS. 1A and 1B, the diaper 100 and the chassis 102 each include a first waist region 116, a second waist region 118, and a crotch region 119 disposed intermediate the first and second waist regions. The first waist region 116 may be configured as a front waist region, and the second waist region 118 may be configured as a back waist region. In some embodiments, the length of each of the front waist region, back waist region, and crotch region may be ⅓ of the length of the absorbent article 100. The absorbent article may also include a laterally extending front waist edge 120 in the front waist region 116 and a longitudinally opposing and laterally extending back waist edge 122 in the back waist region 118. To provide a frame of reference for the present discussion, the diaper 100T in FIGS. 1A and 1B is shown with a longitudinal axis 124 and a lateral axis 126. The longitudinal axis 124 may extend through a midpoint of the front waist edge 120 and through a midpoint of the back waist edge 122. And the lateral axis 126 may extend through a midpoint of a first longitudinal or right side edge 128 and through a midpoint of a second longitudinal or left side edge 130.

As shown in FIGS. 1A and 1B, the diaper 100 includes an inner, wearer facing surface 132, and an outer, garment facing surface 134. As such, it is also to be appreciated that the various components of the diaper described below may each include inner, wearer facing surfaces 132, and an outer, garment facing surfaces 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs, an elastic waist region, and/or flaps, e.g., side panels and/or ears, to enhance the fits around the legs and waist of the wearer, to enhance the fit around the legs of the wearer.

As shown in FIGS. 1A and 1B, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 1A, the laterally extending end edges 144 and 146 may form a portion of the laterally extending front waist edge 120 in the front waist region 116 and a portion of the longitudinally opposing and laterally extending back waist edge 122 in the back waist region 118. The distance between the first lateral end edge 144 and the second lateral end edge 146 may define a pitch length, PL, of the chassis 102. When the diaper 100 is worn on the lower torso of a wearer, the front waist edge 120 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, the user of the diaper 100, including a chassis 102 having a particular size before extension, to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper 100 may include a backsheet 136. The backsheet 136 may also define the outer surface 134 of the chassis 102. The backsheet 136 may be impervious to fluids (e.g., menses, urine, and/or runny feces) and may be manufactured in part from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539, which are all incorporated by reference herein.

As mentioned above, the diaper 100 may also include an absorbent assembly 140 that is joined to the chassis 102. As shown in FIGS. 1A and 1B, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735, which are all incorporated by reference herein.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/0097895 A1, which are all incorporated by reference herein.

As previously mentioned, the diaper 100 may also include elasticized leg cuffs 156 and an elasticized waistband 158. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; and U.S. Patent Publication No. 2009/0312730 A1, which are all incorporated by reference herein.

As shown in FIG. 1B, the chassis 102 may include longitudinally extending and laterally opposing leg cuffs 156 that are disposed on the interior surface 132 of the chassis 102 that faces inwardly toward the wearer and contacts the wearer. Each leg cuff may have a proximal edge. The leg cuffs may also overlap the absorbent assembly 140, wherein the proximal edges extend laterally inward of the respective side edges of the absorbent assembly 152 and 154. In some configurations, the leg cuffs may not overlap the absorbent assembly. It is to be appreciated that the leg cuffs may be formed in various ways, such as for example, by folding portions of the chassis 102 laterally inward, i.e., toward the longitudinal axis 124, to form both the respective leg cuffs and the side edges 128 and 130 of the chassis 102. In another example, the leg cuffs may be formed by attaching an additional layer or layers to the chassis at or adjacent to each of the respective side edges and of the chassis. Each of the leg cuffs may be joined to the interior surface 132 of the chassis and/or the absorbent assembly in leg cuff attachment zones in the front waist region 116 and in leg cuff attachment zones in the back waist region 118. The leg cuffs may extend to the same longitudinal extent as the absorbent article or alternatively the leg cuffs may have a longitudinal extent that is less than the absorbent article.

The elasticized waistband 158 may provide improved fit and containment and may be a portion or zone of the diaper 100 that may elastically expand and contract to dynamically fit a wearer's waist. It is to be appreciated that the elasticized waistband 158 may be located in various positions relative to various diaper components. For example, the elasticized waistband 158 may be positioned longitudinally inwardly from the waist edges 120, 122 of the diaper and/or toward the lateral edges 148, 150 of the absorbent core 142. In some configurations, the elasticized waistband 158 may be positioned with a lateral edge that is coterminous with the waist edges 120, 122. In some configurations, the elasticized waistband 158 may be positioned such that laterally opposing end regions of the waistband 158 are located laterally inward from the leg cuffs 156. In some configurations, the elasticized waistband 158 may be positioned such that laterally opposing end regions of the waistband 158 overlap the leg cuffs 156. In some configurations, the elasticized waistband 158 may be positioned on wearer facing surface 132 of the topsheet 138. In some configurations, the waistband 158 may be positioned on the wearer facing surfaces 132 of the topsheet 138 and the leg cuffs 156. In some configurations, the waistband 158 may be positioned on the wearer facing surfaces 132 of the topsheet 138 and laterally opposing end regions of the waistband 158 may be positioned between the leg cuffs 156 and the topsheet 138. In some configurations, the elasticized waistband 158 may be positioned between the garment facing surface 132 of the topsheet 138 and the wearer facing surface 132 of the backsheet 136. And in some configurations, the elasticized waistband 158 may be positioned on the garment facing surface 134 of the backsheet 136. The diaper 100 may also include more than one elasticized waistband 158, for example, having one waistband 158 positioned in the back waist region 118 and one waistband 158 positioned in the front wait region 116, although other embodiments may be constructed with a single elasticized waistband 158. The elasticized waistband 158 may be constructed in a number of different configurations including those described in U.S. Pat. Nos. 4,515,595 and 5,151,092, which are all incorporated by reference herein.

Taped diapers may be manufactured and provided to consumers in a configuration wherein the front waist region 116 and the back waist region 118 are not fastened, pre-fastened, or connected to each other as packaged, prior to being applied to the wearer. For example, the taped diaper 100 may be folded about a lateral centerline with the interior surface 132 of the first waist region 116 in surface to surface contact with the interior surface 132 of the second waist region 118 without fastening or joining the waist regions together. The rear side panels 104 and 106 and/or the front side panels 108 and 110 may also be folded laterally inward toward the inner surfaces 132 of the waist regions 116 and 118.

It is to be appreciated that the side panels 104, 106, 108, 110 may be assembled in various ways, such as disclosed for example, in U.S. Pat. No. 7,371,302, which is incorporated by reference herein. With continued reference to FIGS. 1A and 1B, each side panel 104, 106, 108, 110 may form a portion of or may be permanently bonded, adhered or otherwise joined directly or indirectly to the chassis 102 laterally inward from the side edges 128 and 130, in one of the front waist region 116 or the back waist region 118. The side panels 104, 106, 108, 110 may also be permanently bonded or joined at or adjacent the side edges 128 and 130 of the chassis 102 in various ways, such as for example, by adhesive bonds, sonic bonds, pressure bonds, thermal bonds or combinations thereof, such as disclosed for example, U.S. Pat. No. 5,702,551, which is incorporated by reference herein.

The diaper 100 may also include various configurations of fastening elements to enable fastening of the front waist region 116 and the back waist region 118 together to form a closed waist circumference and leg openings once the diaper is positioned on a wearer. In some configurations, the rear side panels 104, 106 may be adapted to releasably and/or refastenably engage or connect with another portion of the diaper 100. For example, as shown in FIG. 1A, the diaper 100 may include a connection zone 168, sometimes referred to as a landing zone, in the first waist region 116. As such, when the taped diaper 100 is placed on a wearer, the rear side panels 104, 106 may be pulled around the waist of the wearer such that the fasteners may be connected with the connection zone 168 in the first waist region 116 to form a closed waist circumference and a pair of laterally opposing leg openings. It is to be appreciated that the first and second rear side panels 104, 106 and/or other portions of the diaper, such as the connection zone 168, may include mechanical fasteners in the form of hook and loop fasteners, hook and hook fasteners, macrofasteners, buttons, snaps, tab and slot fasteners, tape fasteners, adhesive fasteners, cohesive fasteners, magnetic fasteners, hermaphroditic fasteners, and the like. Some examples of fastening systems and/or fasteners are discussed in U.S. Pat. Nos. 3,848,594; 4,662,875; 4,846, 815; 4,894,060; 4,946,527; 5,151,092; 5,221,274; 6,251, 097; 6,669,618; 6,432,098; and U.S. Patent Publication Nos. 2007/0078427 A1 and 2007/0093769 A1, which are all incorporated by reference herein.

It is also to be appreciated that the connection zone 168 may be constructed from a separate substrate that is connected with the chassis 102 of the taped diaper. In some configurations, the connection zone 168 may be integrally formed as part of the backsheet 136 of the diaper 100, such as described in U.S. Pat. Nos. 5,735,840 and 5,928,212, which are both incorporated by reference herein. In some configurations, opposing end portions of the connection zone 168 may be integral with and define the first and second front panels 108, 110.

It is to be appreciated that the rear side panels 104, 106 and the connection zone 168 may be constructed from various materials, such as nonwovens, films, and the like, and/or may be constructed as a laminate structure. As shown in FIG. 1B, the rear side panels 104, 106 may include discrete zones 162 of protrusions 164, that may be in the form of hooks 166. In turn, the hooks 166 on the rear side panels 104, 106 may be adapted to releasably and/or refastenably engage or connect with another portion of the diaper 100, such as the connection zone 168. As shown in FIG. 1A, the connection zone 168 may also include discrete zones 162 of protrusions 164 that may be in the form of hooks 166. In turn, the hooks 166 on the connection zone 168 may be adapted to releasably and/or refastenably engage or connect with another portion of the diaper 100, such as the rear side panels 104, 106. As discussed in more detail below, the hooks 166 on the rear side panels 104, 106 and/or the connection zone 168 may be integrally formed from the material of the rear side panels 104, 106 and the connection 168, respectively, such as disclosed in U.S. Pat. Nos. 5,242, 436; 5,325,569; 5,507,736; 6,476,289; 6,478,784; 6,746, 434; and 8,784,722; U.S. Patent Publication No. 2018/ 0141266 A1; and U.S. patent application Ser. No. 16/545, 425, filed on Aug. 20, 2019, which are all incorporated herein by reference.

As previously mentioned, absorbent articles may be assembled with various components that may be constructed with the substrates described herein. Thus, in the context of the previous discussion, the apparatuses and methods herein may be used to form discrete zones of hooks on a substrate while imparting localized speed variances to the substrate while advancing in a machine direction during the assembly of an absorbent article 100. For example, the apparatuses and methods herein may be utilized to form discrete zones 162 of hooks 166 on substrates 200, and in turn, such substrates 200 may be configured as side panels 104, 106, 108, 110, connection zones 168, topsheets 138, and/or backsheets 136 during the manufacture of absorbent articles 100, such as taped diapers and pant diapers for example.

Figure 2:
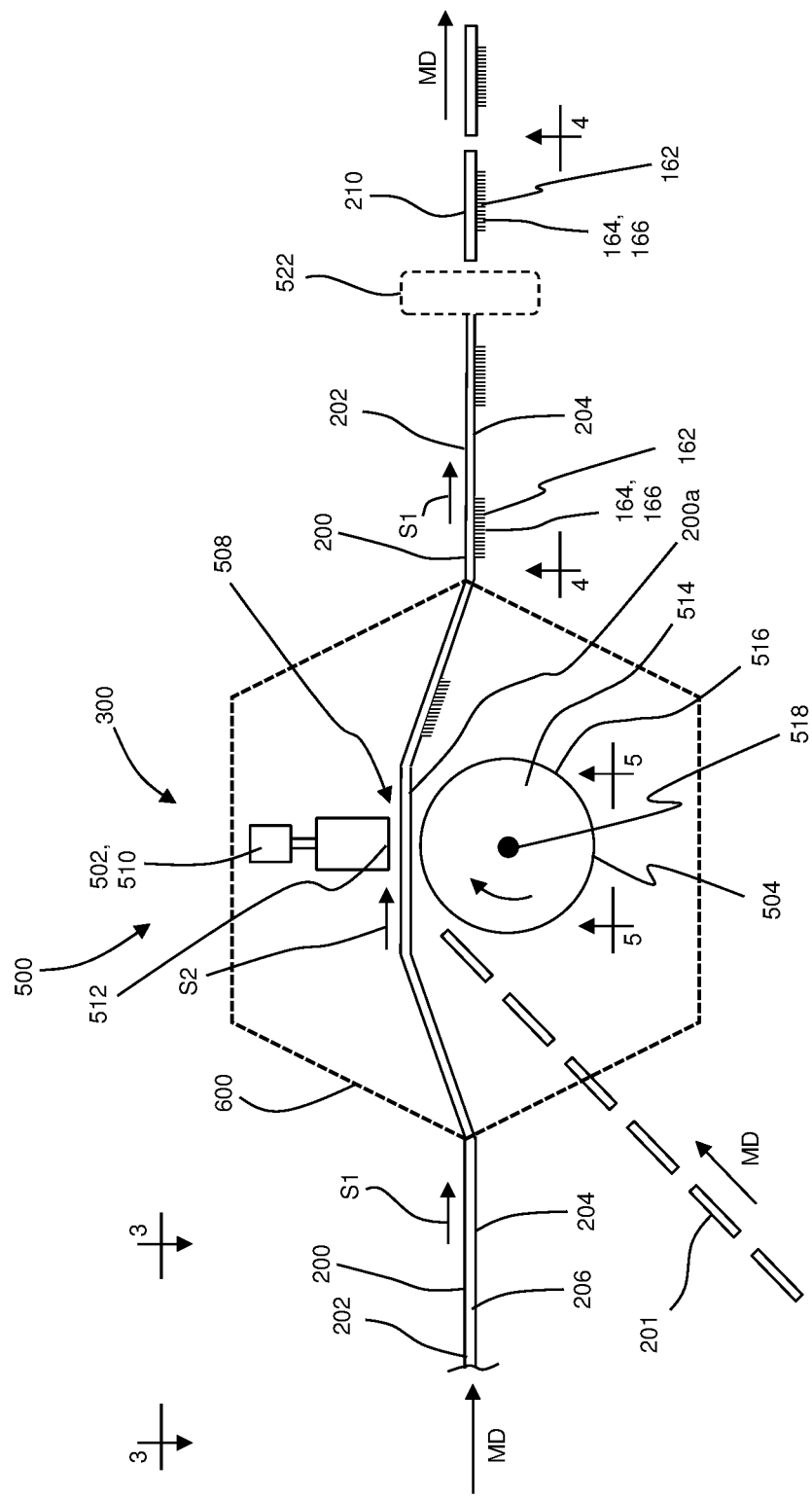
FIG. 2 is a schematic side view of an apparatus for forming protrusions on an advancing substrate.

It is to be appreciated that the systems and methods disclosed herein are applicable to work with various types of converting processes and/or machines. For example, FIG. 2 shows a schematic representation of a converting process including an apparatus or system 300 for forming discrete zones 162 of protrusions 164 on a substrate 200 advancing in a machine direction MD. As shown in FIGS. 2 and 3, the substrate 200 may be a continuous substrate and may include a first surface 202 and an opposing second surface 204. The substrate 200 may also define a width Ws extending in the cross direction CD between a first longitudinal side edge 206 and a second longitudinal side edge 208. Before, during, or after forming the discrete zones 162 of protrusions 164, it is to be appreciated that the substrate 200 may be subjected to additional manufacturing operations, such as combining, bonding, printing, cutting and/or folding operations.

It is also to be appreciated that the substrate 200 may be configured in various ways. For example, the substrate 200 herein may be configured as a single nonwoven substrate or a single film substrate that defines both the first surface 202 and the second surface 204. It is also to be appreciated that the substrate 200 herein may be configured as a laminate including various layers of substrates bonded together, wherein a nonwoven substrate layer defines the first surface 202 and another substrate layer defines the second surface 204. For example, the substrate 200 may include a nonwoven substrate layer or a film substrate layer that defines the first surface 202 and a second substrate layer defining the second surface 204, wherein the second substrate layer may include a nonwoven or a film.

As shown in FIGS. 2-4A, the continuous substrate 200 may advance in a machine direction MD adjacent a protrusion forming apparatus 500 that is configured to form discrete zones 162 of protrusions 164 on the substrate 200. In particular, the protrusion forming apparatus or system 500 comprises an energy source 502 and a die surface 504. As shown in FIG. 5, the die surface comprises cavities 506. As such, the energy source 502 applies energy to the advancing substrate 200 such that softened material of the substrate 200 may be pressed or otherwise move or flow into the cavities 506 of the die surface 504 to form a zone 162 of protrusions 164. In turn, the protrusions 164 are formed directly from and integrally with the material of the substrate 200. It is to be appreciated that various configurations of protrusion forming systems 500 may be used to integrally mold protrusions 164 directly on a substrate 200, wherein the substrate material may serve not only as a structural component material for other purposes, but also as a source of material, such as a polymer for example, for formation of the protrusions 164. Examples of protrusion forming systems 500 are disclosed in U.S. Pat. Nos. 6,478,784; 6,746,434; and 8,784,722; U.S. Patent Publication No. 2018/0141266 A1; and U.S. patent application Ser. No. 16/545,425, filed on Aug. 20, 2019, which are all incorporated herein by reference.

As shown in FIGS. 2-5, the substrate 200 may advance through a nip 508 between the energy source 502 and the die surface 504. The energy source 502 may be configured to heat and/or otherwise apply energy to soften material of the substrate 200 such that the softened material may be pressed or moved into the cavities 506 of the die surface 504 to form protrusions 164 on the substrate 200. In some configurations, the substrate 200 may comprise a nonwoven, and as the nonwoven advances through the nip 508, heating of the polymeric material of the filaments, by application of heating energy, softens the material so that the material may be deformed and forced in the nip 508 and into the cavities 506 of the die surface 504. In some configurations, the die surface 504 may be cooled or otherwise temperature-controlled to help assure that the finished substrate 200 will advance from the nip 508 with formations of protrusions 164 that are stably formed and solidified. The formed protrusions 164 and areas thereof on the substrate 200 will be molded from and thereby physically integral with material(s) of which the nonwoven material and/or laminate is formed. The zone 162 of protrusions 164 may approximately correspond with the arrangement and features of the cavities 506 in the die surface 504.

It is to be appreciated that the energy source 502 may be configured in various ways. For example, as shown in FIG. 2, the energy source may comprise an ultrasonic horn 510 comprising an energy transfer surface 512. As such, ultrasonic horn 510 may be configured to impart ultrasonic energy to the substrate 200 advancing through the nip 508. For example, with reference to FIGS. 2-5, the substrate 200 may advance through the nip 508 such that the second surface 204 of the substrate 200 is arranged in facing relationship with the die surface 504. In turn, the ultrasonic horn 510 may apply energy to the first surface 202 of the substrate 200 advancing through the nip 508. Energy from the ultrasonic horn 510 softens material of the substrate 200 and such softened material moves into the cavities 506 to form protrusions 164 that extend outward from the second surface 204 of the substrate 200. It is to be appreciated that aspects of the ultrasonic horn 510 may be configured in various ways, such as for example linear or rotary type configurations, and such as disclosed for example in U.S. Pat. Nos. 3,113,225; 3,562,041; 3,733,238; 5,110,403; 6,036,796; 6,508,641; and 6,645,330, all of which are incorporated by reference herein. In some configurations, the ultrasonic horn 510 may be configured as a linear oscillating type sonotrode, such as for example, available from Herrmann Ultrasonic, Inc. In some configurations, the sonotrode may include a plurality of sonotrodes nested together in the cross direction CD.

It is to be appreciated that the die surface 504 and/or the cavities 506 therein may be configured in various ways. For example, the protrusion forming apparatus 500 may include a roll 514 comprising an outer circumferential 516 surface adapted to rotate about an axis 518 of rotation. In turn, the die surface 504 may be formed to define a portion of the outer circumferential surface 516 of the roll 514. During protrusion forming operations, the substrate 200 may advance through the nip 508 with the second surface 204 in a facing relationship with the outer circumferential surface 516 of the rotating roll 514. It is to be appreciated that the roll 514 may define various cross sectional shapes, such circular or oblong and/or may be configured to constantly or intermittently contact the substrate 200 advancing through nip 508.

As shown in FIG. 5, the cavities 506 may be arranged in regions that correspond with the shapes and/or size of the zones 162 of the protrusions 164 formed on the substrate 200. In some configurations, the cavities 506 may be arranged circumferentially on the roll 514 in various ways to define different shapes and/or sizes of regions capable of forming different sizes and/or shapes of zones 162 of protrusions 164 on the substrate 200. In some configurations, the cavities 506 may be integrally formed in the outer circumferential surface 516 of the roll 514. The roll 514 may also be configured with various features to help provide flexible arrangements to more easily accommodate desired changes in shapes, sizes, and/or locations of the zones 162 of protrusions 164 on the substrates 200 and/or the shapes and/or densities of the protrusions 164. For example, the roll 514 may be connected with a motor, such as a servo motor, adapted to rotate the roll 514 at constant and/or variable angular velocities. The ability to rotate at variable angular velocities may help provide for adjustment of desired machine direction MD spacing between zones 162 of protrusions 164 on the substrate 200 without the need to replace the roll and/or associated components. In some configurations, the die surface 504 and cavities 506 may be defined by parts 520 that may be releasably and/or otherwise movably connected with the roll 504, such as shown in FIG. 5. For example, such parts 520 may be selectively movable axially and/or circumferentially on the roll 514. Such movable parts 520 may help provide for adjustment of desired machine direction MD spacing between zones 162 of protrusions 164 on the substrate 200 and/or cross directional CD position of zones 162 of protrusions 164 on the substrate 200 without the need to replace the roll 504 and/or associated components. Such releasably connectable and replaceable parts 520 may also help provide the ability to change the shapes and/or sizes of zones 162 of protrusions 164 and/or densities and/or types of protrusions 164 to be formed on a substrate 200 without the need to replace the entire roll 504.

As previously mentioned, it is to be appreciated the protrusion forming system 500 may be configured to form different types and/or shapes of protrusions 164 on the substrate. As shown in FIGS. 2 and 4A, the protrusions 164 may be formed to protrude from the second surface 204 of the substrate 200 to a distal end 165. In some configurations, such as shown in FIG. 4A for example, the protrusions 164 may be formed as hooks 166. Various examples of protrusion and hook shapes are disclosed in U.S. Pat. Nos. 6,478,784; 6,746,434; and 8,784,722; U.S. Patent Publication No. 2018/0141266 A1; and U.S. patent application Ser. No. 16/545,425, filed on Aug. 20, 2019, which are all incorporated herein by reference.

With continued reference to FIGS. 2 and 4, the zones 162 of protrusions 164 may extend a maximum length $L_Z$ in the machine direction MD and may extend a maximum width $W_Z$ in the cross direction CD. As shown in FIG. 4, the discrete zones 162 of protrusions 164 may be separated from each other in the machine direction MD, and one or more discrete zones 162 of protrusions 164 may be formed on the substrate 200 in the cross direction CD. It is also to be appreciated the width $W_Z$ of the zones 162 may be equal to or less than the width $W_s$ of the substrate 200. As previously mentioned, the zones 162 may comprise the same or different sizes and/or shapes and/or protrusion densities.

As previously mentioned, the protrusion forming systems 500 referred to herein may necessitate relatively slow substrate 200 advancement speeds in order to provide adequate time to perform the protrusion forming operations. Thus, in some configurations where the substrate 200 may be incorporated to other assembly processes, such as absorbent article manufacturing lines, operating at relatively high speed production rates, it may be necessary to temporarily slow the substrate 200 when advancing through the protrusion forming system 500. Referring again FIG. 2, the substrate 200 may advance through an accumulator apparatus 600 that decelerates a portion 200*a* of the substrate 200 to a second speed S2 less than first speed S1. While at the second speed S2, a protrusion forming system 500 may operate to form discrete zones 162 of protrusions 164 on the second surface 204 of the portion 200*a* of the substrate 200. Once the zone 162 of protrusions 164 is formed, the portion 200*a* of the substrate 200 is accelerated back to the first speed S1 and exits the accumulator apparatus 600. In some configurations, the accumulator system 600 may operate to temporarily accelerate the portion 200*a* of the substrate 200 to speeds greater than the first speed S1 before decelerating the portion 200*a* of the substrate 200 back to the first speed S1.

Figure 6:
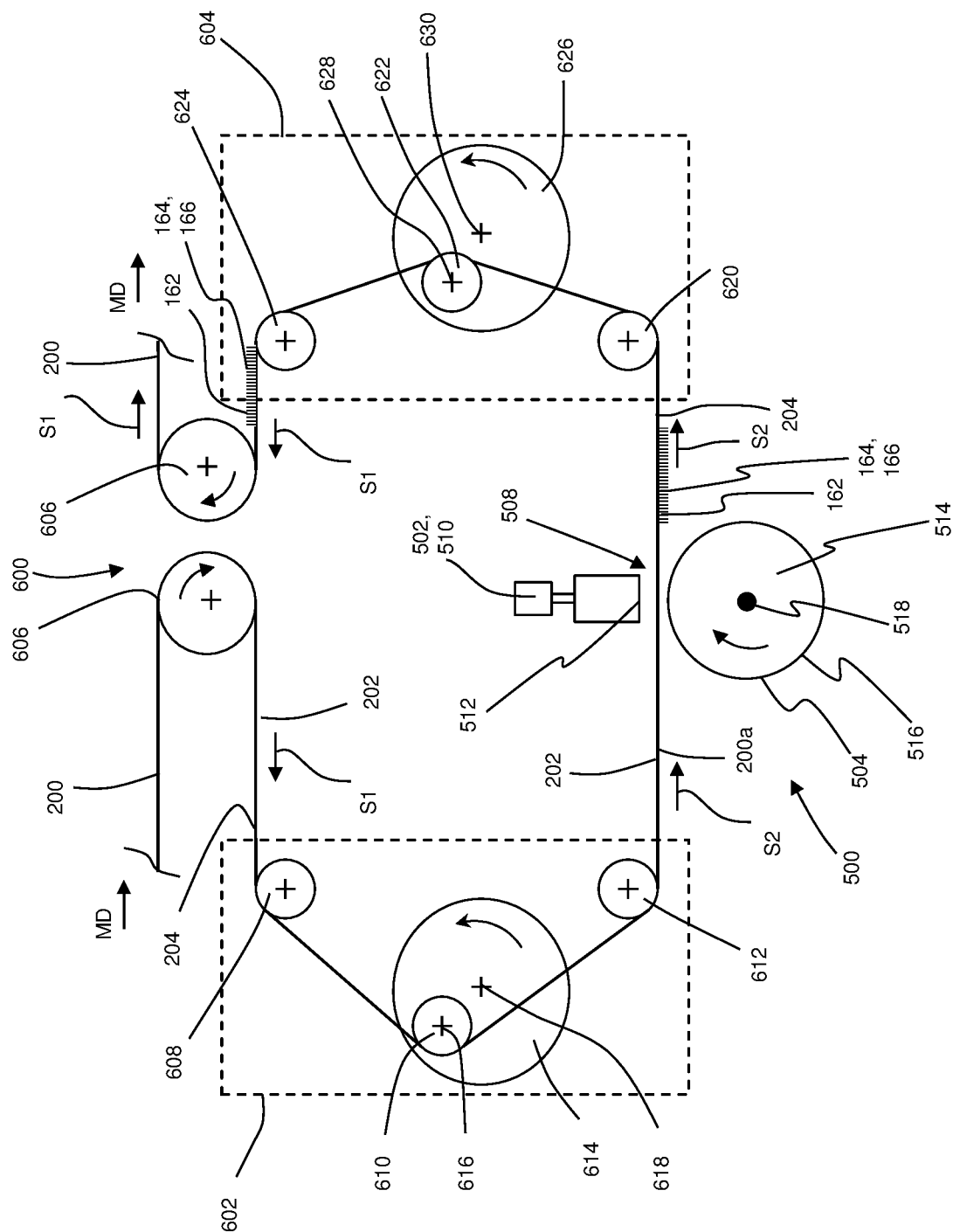
FIG. 6 is a detailed view of an accumulator apparatus.

As previously mentioned, the processing lines herein 300 may include an accumulator apparatus 600 that decelerates a portion 200*a* of an advancing substrate 200 from a first speed S1 to a second speed S2 while advancing past the protrusion forming system 500. It is to be appreciated that the accumulator apparatus 600 may be configured in various ways for example such as disclosed in U.S. Pat. Nos. 5,373,761; 5,693,165; 6,596,108; 6,620,276; 6,349,867; and 8,377,249. For example, FIG. 6 shows an example accumulator apparatus 600 for varying the speed of the advancing substrate 200. As such, the apparatus 600 may be configured to provide localized speed changes of the substrate 200. For example, the apparatus 600 may provide localized speed changes of the substrate 200 as the substrate 200 advances past the protrusion forming system 500.

As shown in FIG. 6, the apparatus 600 may include a first substrate guide 602 and a second substrate guide 604. The substrate 200 advances in the machine direction MD around an idler roller 606, and enters the first substrate guide 602 at a first speed S1. The substrate 200 travels from the first substrate guide 602 at a second speed S2 past the protrusion forming system 500. From the protrusion forming system 500, the substrate 200 enters the second substrate guide 604. The substrate 200 then exits the second substrate guide 604 at the first speed S1. As discussed in more detail below, the first substrate guide 602 and second substrate guide 604 operate to change the lengths of the substrate 200 within the respective guides, and thus, vary the second speed S2 of the substrate 200 traveling from the upstream, first substrate guide 602 to the downstream, second substrate guide 604. At the same time, the speed of the substrate 200 entering the first substrate guide 602 and exiting the second substrate guide 604 is maintained at a constant first speed S1. The idler rollers 606 in FIG. 6 show only one example of how the substrate 200 may be advanced to and from the apparatus 600, and as such, it is to be appreciated that various other configurations and arrangements can be utilized.

As previously mentioned, the second speed S2 of the substrate 200 can be varied as the substrate 200 travels past the protrusion forming system 500. As discussed in more detail below, the first and second substrate guides 602, 604 may be configured to periodically slow (e.g. second speed, S2, is slower than the first speed, S1) the movement of the portion 200*a* of the substrate 200 in the machine direction MD advancing past the protrusion forming system 500. In some configurations, the first and second substrate guides 602, 604 may be configured to periodically stop (e.g. second speed, S2, is zero) the movement of the portion 200*a* of the substrate 200 in the machine direction MD advancing past the protrusion forming system.

As described in more detail below, the substrate guides 602, 604 may be configured to touch only one side of the substrate 200. For example, the first and second substrate guides 602, 604 may be configured to touch only the first surface 202 of the substrate 200, and do not touch the second surface 204 of the substrate 200. Such a configuration may be beneficial to reduce negative impacts on the protrusion forming operations performed on the substrate 200. For example, FIG. 6 shows the protrusion forming system as forming protrusions on the second surface 204 of the substrate 200 before the substrate 200 enters the second substrate guide 604. Because the first and second substrate guides 602, 604 touch only the first surface 202 of the substrate 200, risks of contaminating or otherwise affecting the newly formed protrusions 164 on the second surface 204 of the substrate 200 may be reduced.

With continued reference to FIG. 6, the first substrate guide 602 includes a first guide member 608 in the form of a first roller, a second guide member 610 in the form of a second roller, and a third guide member 612 in the form of a third roller. As described below, the substrate 200 travels in the machine direction MD at the first speed S1 to the first roller 608; from the first roller 608 to the second roller 610; from the second roller 610 to the third roller 612; and from the third roller 612 to the protrusion forming system 500 and to the second substrate guide 604 at the second speed S2. As shown in FIG. 6, the second roller 610 is rotatably connected with a support member 614 at a second roller axis 616. The support member 614 is adapted to rotate around a second center axis 618. As such, the second roller 610 orbits around the second center axis 618 as the support member 614 rotates. As the substrate 200 advances through the first substrate guide 602, only the first surface 202 of the substrate 200 contacts the outer radial surfaces of the first, second, and third rollers 608, 610, 612.

Similar to the first substrate guide 602, the second substrate guide 604 includes a first guide member 620 in the form of a first roller, a second guide member 622 in the form of a second roller, and a third guide member 624 in the form of a third roller. As described below, the substrate 200 travels in the machine direction MD at the second speed S2 (from the first substrate guide 602 and past the protrusion forming station 500 to the first roller 620; from the first roller 620 to the second roller 622; from the second roller 622 to the third roller 624; and from the third roller 624 to continue downstream at the first speed S1. As shown in FIG. 6, the second roller 622 is rotatably connected with a support member 626 at a second roller axis 628. The support member 626 is adapted to rotate around a second center axis 630. As such, the second roller 622 orbits around the second center axis 630 as the support member 626 rotates. As the substrate 200 advances through the second substrate guide 604, only the first surface 202 of the substrate 200 contacts the outer radial surfaces of the first, second, and third rollers 620, 622, 624.

Although the guide members 608, 610, 612, 620, 622, 624 of the first and second substrate guides 602, 604 are shown and described as rollers, it is to be appreciated that the guide members can be configured in other ways. For example, in some embodiments, the guide members may be configured as rollers, stationary pins or rods, endless belts, spheres, and/or combinations thereof. In addition, although the support members 614, 626 are shown in the form of wheels, it is to be appreciated that the support members may be configured in other ways, such as for example, an elongate member or rotating arm. Further, some or all of the rollers can be driven rollers, idler rollers, and/or combinations of each. In addition, the support members can be rotated at constant or variable speeds. In some embodiments, the support members 614, 626 may have separate and/or variable speed drives, such as for example, servo motors.

As mentioned above with reference to FIG. 6, the first substrate guide 602 and the second substrate guide 604 utilize orbital motion of guide members to change the length of the substrate 200 within the substrate guides. In particular, rotation of the support members 614, 626 causes the second rollers 610, 622 to orbit around the second center axes 618, 630. In turn, the orbital motions of the second rollers 610, 622 result in changes of the lengths of substrate within the substrate guides 602, 604. As such, the coordinated rotation of the support members 614, 626 of the first and second substrate guides 602, 604 result in localized speed changes of the substrate 200 advancing past the protrusion forming system 500 (i.e. a variable second speed, S2), while maintaining a constant first speed, S1.

It is to be appreciated that the protrusion forming apparatus 500 may be configured in various ways to help assure that the finished substrate 200 includes protrusions 164 that are stably formed and solidified. In some configurations, the forming apparatus 500 may be configured to help maintain contact between the substrate 200 and the die surface 504 for relatively longer periods of time to provide the protrusions 164 additional time to cool before advancing from the die surface 504. For example, the forming apparatus 500 shown in FIG. 6A may be configured such that during protrusion forming operations, the substrate 200 may be partially wrapped onto the roll 514. As such, a length of the substrate 200 may remain in contact with the outer circumferential surface 516 of the roll 514 after advancing from the nip 508. Thus, the protrusions 164 may be provided some additional time to cool before the substrate 200 advances from the outer circumferential surface 516 of the roll 514. In some configurations, the forming apparatus may include rolls 550 to guide the substrate 200 onto the outer circumferential surface 516 of the roll 514.

As previously mentioned, the die surface 504 may also be cooled or otherwise temperature-controlled. As such, it is to be appreciated that the outer circumferential surface 516 of the roll 514 shown in FIG. 6A may also be adapted to the cool the substrate 200 after advancing from the nip 508 and before advancing from the outer circumferential surface 516. In some configurations, the outer circumferential surface 516 may also be adapted to pre-heat the substrate 200 before advancing to the nip 508.

Figure 6A:
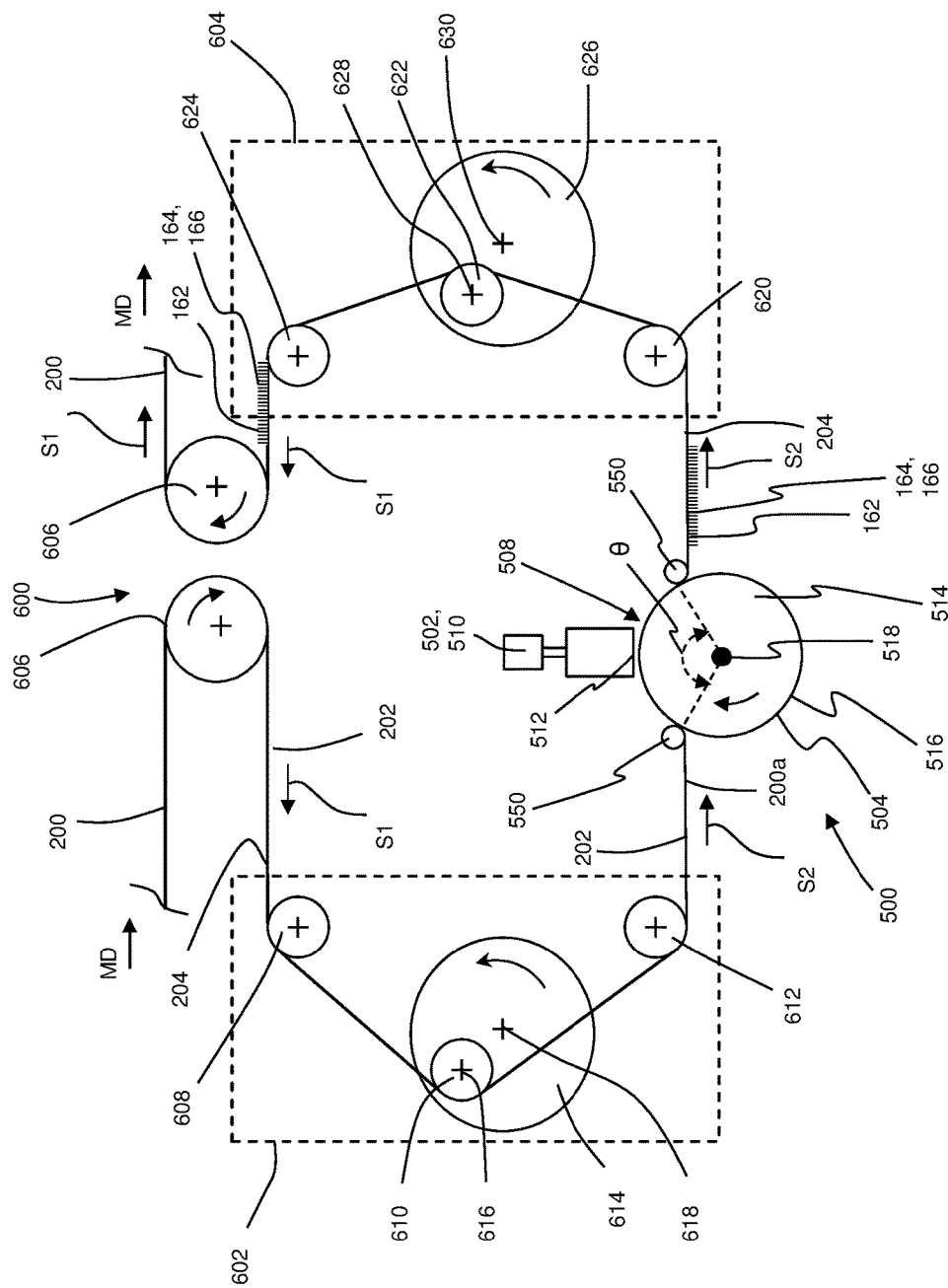
FIG. 6A is a detailed view of an accumulator apparatus with a substrate partially wrapped onto a roll.

As shown in FIG. 6A, the extent that the substrate 200 wraps around the roll 514 may be referred to herein as the wrap angle, θ, and may be expressed in units of degrees. In some configurations, the wrap angle, θ, may be greater than zero degrees and less than or equal to 180 degrees, specifically reciting all 1 degree increments within the above-recited range and all ranges formed therein or thereby. In some configurations, the wrap angle, θ, may be greater 180 degrees.

With continued reference to FIG. 6A, the roll 514 may also be configured to rotate at variable angular velocities such that speed of the outer circumferential surface 516 matches or substantially matches the speed profile of the portion 200a of the substrate 200 that is decelerated and accelerated by the accumulator apparatus 600. For example, the roll 514 may be connected with a servo motor that may rotate the roll 514 at constant and/or variable angular velocities in conjunction with the varying speeds of the portion 200a of the substrate 200.

Figure 7:
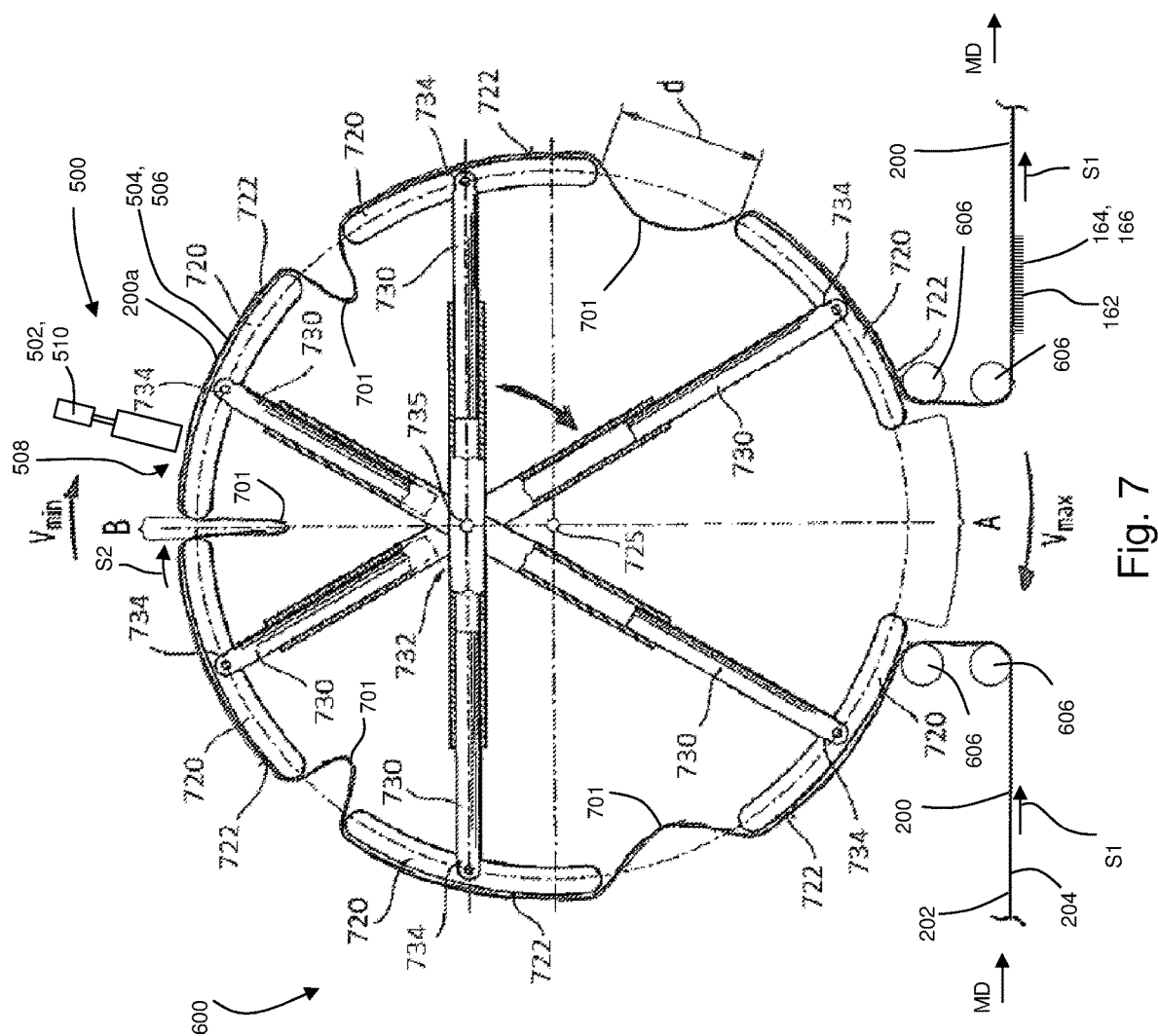
FIG. 7 is a detailed view of a second configuration of an accumulator apparatus.

FIG. 7 shows another example of an accumulator apparatus 600 for varying the speed of the advancing substrate 200 similar to the apparatus disclosed in U.S. Pat. No. 6,620,276, which is incorporated by reference herein. As such, the apparatus 600 may be configured to provide localized speed changes of the substrate 200 as the substrate 200 advances past the protrusion forming station 500. As shown in FIG. 7, the accumulator apparatus 600 includes web support plates 720 connected with extendible arms 730, wherein each web support plate 720 comprises a web support surface 722 facing outwardly. The web support plates 720 may be configured as the die surface 504 wherein the web support surface 722 of each web support plate 720 may include cavities 506, such as described above. As discussed in more detail below, the extendible arms 730 rotate the support plates 720 such that the web support surfaces 722 trace out an essentially circular path around a principal axis 725. Each extendible arm 730 has a proximal end 732 and a distal end 734, the proximal end 732 of each extendible arm 730 rotatably connected with a second axis of rotation 735 and the distal end 734 of each extendible arm 730 being pivotally connected with a web support plate 720.

As shown in FIG. 7, the principal axis 725 and the second axis 735 are parallel and off-set in relation to each other, and as such, the extendible arms 730 drive the web support plates 720 around the circular path with a variable circumferential velocity. As a web support plate 720 passes through point A of the circular path (at the bottom of the circular path as illustrated in FIG. 7), the web support plate 720 has a maximum circumferential velocity Vmax. As the web support plate 720 is rotated towards the top of the circular path, the web support plate 720 is decelerated until reaching a minimum circumferential velocity Vmin at point B of the circular path. As the web support plate 720 continues around the circular path, the web support plate 720 is accelerated again to Vmax while returning to point A. Also, as shown in FIG. 7, adjacent web support plates 720 are spaced apart by a distance d. The adjacent web support plates either side of point A in FIG. 7 have a maximum distance d between each other. As the web support plates 720 are rotated, one of the web support plates 720 has a faster circumferential velocity than an adjacent web support plate, and the faster web support plate catches up with the slower web support plate, thereby reducing the distance d between the adjacent web support plates 720. The adjacent web support plates either side of point B in FIG. 7 have a minimum distance d between each other.

With continued reference to FIG. 7, the substrate 200 advances in the machine direction MD at a first speed S1 around two idler rollers 606, and onto the web support surfaces 722 of the rotating web support plates 720. As the substrate 200 is advanced around the circular path by the decelerating web support plates 720, loops 701 are formed between adjacent web support plates 720. As the web support plates rotate, a portion 200a of the substrate 200 advances past the protrusion forming station 500 at the second speed $S_2$, wherein S2 is less than S1. As previously mentioned, the web support plates 720 may be configured as the die surface 504 wherein the web support surface 722 of each web support plate 720 may include cavities 506. As such, the portion 200a of the substrate 200 advances at the second speed $S_2$ through the nip 508 defined between the energy source 502 and the die surface 504. The energy source 502 applies energy to the substrate 200 as described above to form zones 162 of protrusions 164. Subsequently, the web support plates 720 and substrate 200 accelerate, thereby removing the loops between adjacent web support plates 720. The substrate 200 then advances from the support plates 720 at the first speed S1 around two idler rollers 606, and onto the remainder of the assembly process.

As previously mentioned, the zones 162 of protrusions 164 may be formed on a portion 200a of the substrate 200 while advancing at a second speed S2, wherein the second speed S2 is less than the first speed S1. It is to be appreciated that system may be configured with various relative differences between the first speed and second speeds. For example, in some configurations, the second speed S2 is from about 25% to about 50% of the first speed S1. In some configurations, the second speed S2 is about 25% of the first speed S1.

Figure 4B:
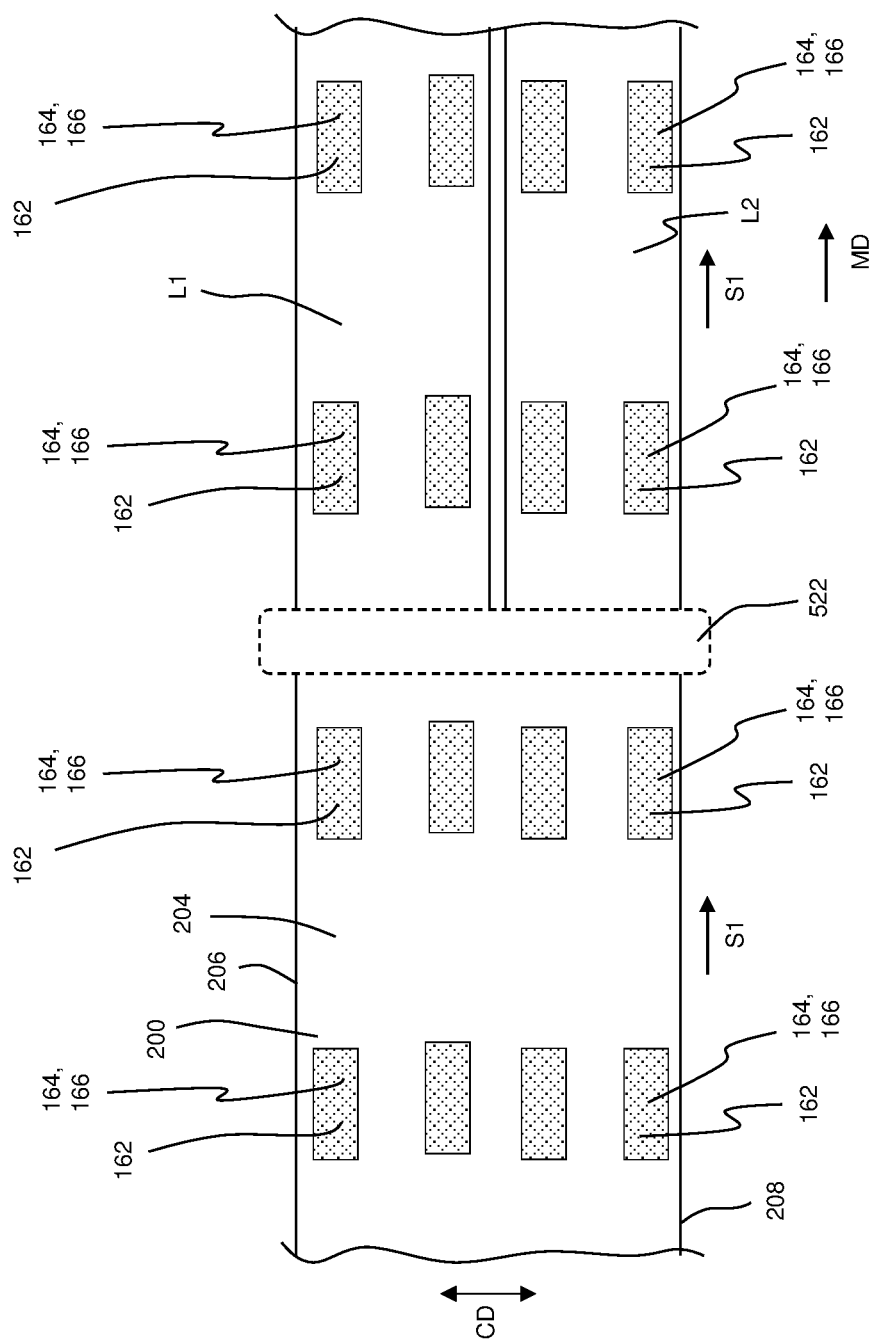
FIG. 4B is a view of an advancing substrate with discrete zones of protrusions being slit along the machine direction into multiple lanes.

It is to be appreciated that the protrusion forming operations may be performed separate to product assembly processes, such as for example, forming protrusions 164 on the substrates 200 offline wherein the substrates 200 may be stored until needed for production. For example, protrusion forming operations may be accomplished on discrete forming lines, separately from converting lines that are dedicated to manufacturing products such as absorbent articles. After forming the protrusions 164 on the forming lines, the substrates 200 may be delivered to the converting lines, such as in a form of continuous webs comprising protrusions formed thereon. In addition to or alternatively to offline protrusion forming operations, protrusion forming operations may be done online during article assembly processes. As previously mentioned, the substrate 200 may advance from the protrusion forming apparatus 500 and may be subjected to additional manufacturing operations, such as combining, bonding, printing, cutting and/or folding operations. For example, as shown in FIGS. 2 and 4, the substrate 200 with the protrusions formed thereon may advance to a cutter apparatus 522 that separates the continuous substrate 200 into separate the pieces 210. The cutter apparatus 522 is generically represented by dashed rectangle in FIGS. 2 and 4. It is to be appreciated the cutter apparatus 522 may be configured in various ways, such as for example, a knife roll and anvil roll. In another example, the cutter apparatus 522 may include a laser adapted to cut the discrete parts 210 from the continuous substrate 200. As shown in FIG. 4, the substrate 200 may be into discrete pieces 210 each having a pitch length, PL, extending along the machine direction MD wherein the length, Lz, of the zone 162 of protrusions 164 extends in the machine direction MD for less than the pitch length, PL. It is also be appreciated that the cutter apparatus 522 may be configured to slit or cut the substrate 200 along the machine direction MD to create two or more lanes L1, L2 of continuous substrates having protrusions 164 formed thereon, such as shown in FIG. 4B.

It is also to be appreciated that the protrusion forming operations may be performed in conjunction with bonding operations. For example, the roll 514 and ultrasonic horn 510 described above may be configured to perform the protrusion forming process and bonding processes simultaneously. In some configurations, such as shown in FIG. 5A, the roll 514 may include cavities 506 capable of interacting with the energy source 502 to form the protrusions 164 as described above. In addition to the cavities 506, the outer circumferential surface 516 of the roll 514 may also comprise one or more bonding surfaces 524 defined by bonding elements 526 extending radially outward from the outer circumferential surface 516. As shown in FIG. 2, as the roll 514 rotates, the substrate 200 and a second substrate 201 may be advanced between the bonding surfaces 524 and the energy source 502 to mechanically bond or weld the substrate 200 and the second substrate 201 together to create bond regions between the between the two substrates 200, 201. It is to be appreciated that the second substrate 201 may be positioned in a facing relationship with either the first surface 202 or the second surface 204 of the substrate 200 during bonding. Heat and/or pressure between the energy source 502 and the roll 514 may melt and bond the substrates 200, 201 together in areas supported by the bonding surfaces 524 on the roll 514. As such, the mechanical bonds and/or bond regions may have shapes that correspond with and may mirror shapes of the bonding surfaces 524. In some configurations, the bonding and protrusion forming operations may be done with the same energy source, such as the same ultrasonic horn. In some configurations, the bonding and protrusion forming operations may be done with different energy sources, such as different ultrasonic horns. It is to be appreciated that the bonding operations may also be configured in various ways, such as with heated or unheated pattern rolls, anvil rolls and/or ultrasonic bonding devices. It is to be appreciated that the roll 514 and/or energy source 502 may be configured to apply heat and pressure in various ways to perform mechanical bonding, such as for example, the mechanical bonding devices and methods disclosed in in U.S. Pat. Nos. 4,854,984; 6,248,195; 8,778,127; 9,005,392; 9,962,297; and 10,052,237, all of which are incorporated by reference herein.

It is to be appreciated that the second substrate 201 illustrated in FIG. 2 may be configured to be continuous or discrete lengths. It is also to be appreciated that the second substrate 201 and/or additional substrates may be combined with and/or bonded with the substrate 200 before, during, or subsequent to the protrusion forming operations. In addition, the second substrate 201 may be configured as an absorbent article component such as described above with reference to FIGS. 1A and 1B. For example, in some configurations, the second substrate 201 may be configured as a continuous or discrete chassis 102, topsheet 138, and/or backsheet 136 and the substrate 200 may be configured as a connection zone 138 or side panels 104, 106, 108, 110.

In yet other configurations, the apparatus 300 may be configured with one or more adhesive applicator devices adapted to apply adhesive to bond substrates 200, 201 together with the applied adhesive. It is to be appreciated that such adhesive applicator devices may be configured in various ways, such as for example, as a spray nozzle and/or a slot coating device. In some configurations, the adhesive applicator device may be configured in accordance with the apparatuses and/or methods disclosed in U.S. Pat. Nos. 8,186,296; 9,265,672; 9,248,054; and 9,295,590 and U.S. Patent Publication No. 2014/0148773 A1, which are all incorporated by reference herein. It is also to be appreciated that adhesive may be applied to create the bond regions in conjunction with or instead of the mechanical bonding processes discussed above.

It is also to be appreciated that the protrusion forming operations herein may also be performed in conjunction with other operations, such as printing operations. For example, print stations may be configured to print either or both the first surface 202 and the second surface 204 of the substrate 200 before or after forming the zones 162 of protrusions 164 thereon. It is to be appreciated that the printing stations may be configured in various ways and may include various types of printing accessories. For example, the printing stations may be capable of printing ink on substrate materials to form graphics by various printing methods, such as flexographic printing, rotogravure printing, screen-printing, inkjet printing, and the like. In some configurations, one or more lasers may be provided to create laser induced graphics on either or both the first surface 202 and the second surface 204 of the substrate 200. It is to be appreciated that graphics may be positioned inside and/or outside areas of the substrate 200 where zones of protrusions have been or will be formed.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling absorbent articles, the method comprising steps of:
    advancing a first substrate in a machine direction at a first speed, the first substrate comprising a first surface and an opposing second surface and defining a width, Ws, in a cross direction;
    decelerating a portion of the first substrate to a second speed;
    arranging the second surface of the portion the first substrate and a die surface in a facing relationship, wherein the die surface comprises cavities;
    applying energy to the portion of the first substrate while advancing at the second speed such that softened material of the first substrate moves into the cavities of the die surface to form a zone of protrusions, wherein the zone of protrusions extends in the machine direction for a length, Lz, wherein each protrusion protrudes from the second surface of the first substrate to a distal end, and wherein the protrusions comprise hooks;
    accelerating the portion of the first substrate with the zone of protrusions from the second speed to the first speed; and
    cutting the first substrate into discrete pieces each having a pitch length, PL, extending along the machine direction, wherein the length, Lz, of the zone of protrusions extends in the machine direction for less than the pitch length, PL.

2. The method of claim 1, further comprising repeating the steps of decelerating, arranging, applying, and accelerating to form a plurality of zones of protrusions separated from each other along the machine direction.

3. The method of claim 1, wherein the first substrate comprises a nonwoven.

4. The method of claim 1, wherein the step of applying energy further comprises contacting the first surface of the first substrate with an energy transfer surface of an ultrasonic horn.

5. The method of claim 4, wherein the ultrasonic horn comprises a linear horn.

6. The method of claim 4, wherein the ultrasonic horn comprises a rotary horn.

7. The method of claim 1, wherein the die surface comprises an outer circumferential surface of a roll.

8. The method of claim 7, further comprising a step of rotating the roll.

9. The method of claim 8, wherein the step of rotating the roll further comprises rotating the roll at a variable angular velocity.

10. The method of claim 8, wherein the step of rotating the roll further comprises intermittently contacting the die surface with the first substrate.

11. The method of claim 7, wherein a position of the die surface is adjustable in the cross direction.

12. The method of claim 1, further comprising steps of:
    combining a second substrate with the portion of the first substrate; and
    bonding the second substrate with the portion of the first substrate while at the second speed.

13. The method of claim 12, wherein step of the applying energy further comprises applying energy to the first substrate and the second substrate.

14. A method for assembling absorbent articles, the method comprising steps of:
    advancing a first substrate in a machine direction at a first speed, the first substrate comprising a first surface and an opposing second surface and defining a width, Ws, in a cross direction;
    decelerating a portion of the first substrate to a second speed;
    arranging the second surface of the portion the first substrate and a die surface in a facing relationship, wherein the die surface comprises cavities;
    applying energy to the portion of the first substrate while advancing at the second speed such that softened material of the first substrate moves into the cavities of the die surface to form a zone of protrusions, wherein the zone of protrusions extends in the cross direction for a width, Wz, wherein each protrusion protrudes from the second surface of the first substrate to a distal end, and wherein the protrusions comprise hooks;
    accelerating the portion of the first substrate with the zone of protrusions from the second speed to the first speed; and
    cutting the first substrate into discrete pieces, wherein the width, Wz, of the zone of protrusions extends in the cross direction for a distance that is equal to or less than the width, Ws.

15. The method of claim 14, further comprising repeating the steps of decelerating, arranging, applying, and accelerating to form a plurality of zones of protrusions separated from each other along the machine direction.

16. The method of claim 14, wherein the step of applying energy further comprises contacting the first surface of the first substrate with an energy transfer surface of an ultrasonic horn.

17. A method for assembling absorbent articles, the method comprising steps of:
- advancing a first substrate in a machine direction at a first speed, the first substrate comprising a first surface and an opposing second surface and defining a width, W, in a cross direction;
- decelerating a portion of the first substrate to a second speed;
- arranging the second surface of the portion the first substrate and a die surface in a facing relationship, wherein the die surface comprises cavities;
- applying energy to the portion of the first substrate while advancing at the second speed such that softened material of the first substrate moves into the cavities of the die surface to form a zone of protrusions, wherein the zone of protrusions extends in the machine direction for a length, Lz, wherein each protrusion protrudes from the second surface of the first substrate to a distal end, and wherein the protrusions comprise hooks;
- combining a second substrate with the portion of the first substrate;
- bonding the second substrate with the portion of the first substrate while at the second speed;
- accelerating the second substrate and the portion of the first substrate with the zone of protrusions from the second speed to the first speed; and
- cutting the first substrate into discrete pieces.

18. The method of claim 17, wherein step of the applying energy further comprises applying energy to the first substrate and the second substrate.

* * * * *